United States Patent [19]

Teitz et al.

[11] Patent Number: 5,419,772
[45] Date of Patent: May 30, 1995

[54] SURGICAL IRRIGATION APPARATUS FOR CLEANING AND STERILIZING WOUNDS AND SURGICAL AREAS DURING SURGERY

[76] Inventors: Bernard R. Teitz, 1822 Belmont Dr., Green Oaks, Ill. 60048; Michael Bamberger, 9255 N. Pelham Pkwy., Milwaukee, Wis. 53217

[21] Appl. No.: 129,859
[22] Filed: Sep. 29, 1993
[51] Int. Cl.6 .................. A61M 1/00; A61M 37/00
[52] U.S. Cl. .................. 604/141; 604/142; 604/146; 604/147; 604/249; 128/DIG. 12
[58] Field of Search ............... 604/19, 33–39, 604/43, 48, 49, 51, 54, 55, 141, 142, 146, 147, 249, 257, 259; 128/DIG. 12; 222/498

[56] References Cited

U.S. PATENT DOCUMENTS

| | | | |
|---|---|---|---|
| 1,845,343 | 2/1932 | Salerni . | |
| 3,071,402 | 1/1963 | Lasto et al. | 294/64 |
| 3,153,414 | 10/1964 | Beall et al. | 604/142 |
| 3,208,145 | 9/1965 | Turner | 32/33 |
| 3,429,313 | 2/1969 | Romanelli . | |
| 3,626,959 | 12/1971 | Santomieri | 137/1 |
| 3,640,277 | 2/1972 | Adelberg | 604/141 |
| 3,645,497 | 2/1972 | Nyboer | 251/148 |
| 3,674,024 | 7/1972 | Crillo | 128/234 |
| 3,749,090 | 7/1973 | Stewart | 128/240 |
| 3,834,388 | 9/1974 | Sauer | 128/276 |
| 3,847,371 | 11/1974 | Norton et al. | 251/65 |
| 3,889,675 | 6/1975 | Stewart | 128/240 |
| 3,929,126 | 12/1975 | Corsaut | 128/240 |
| 3,964,484 | 6/1976 | Reynolds et al. | 128/276 |
| 4,090,514 | 5/1978 | Hinck et al. | 128/214 |
| 4,299,221 | 11/1981 | Phillips et al. | 128/276 |
| 4,397,640 | 9/1983 | Haug et al. | 604/33 |
| 4,508,532 | 4/1985 | Drews | 604/22 |
| 4,526,573 | 7/1985 | Lester | 604/33 |
| 4,539,005 | 9/1985 | Greenblatt | 604/141 |
| 4,551,129 | 11/1985 | Coleman | 604/21 |
| 4,562,838 | 1/1986 | Walker | 604/35 |
| 4,573,979 | 3/1986 | Blake | 604/240 |
| 4,576,593 | 3/1986 | Mommer | 604/250 |
| 4,626,243 | 12/1986 | Singh et al. | 604/141 |
| 4,642,090 | 2/1987 | Utrata | 604/22 |
| 4,668,215 | 5/1987 | Allgood | 604/30 |
| 4,676,779 | 6/1987 | Mayoral | 604/65 |
| 4,680,026 | 7/1987 | Weightmann | 604/3 |
| 4,690,762 | 9/1987 | Katsura et al. | 210/436 |
| 4,705,500 | 11/1987 | Reimels | 604/35 |
| 4,764,165 | 8/1988 | Reimels | 604/22 |
| 4,787,889 | 11/1988 | Steppe | 604/22 |
| 4,787,891 | 11/1988 | Levin | 604/136 |
| 4,913,698 | 4/1990 | Ito et al. | 604/22 |
| 4,941,872 | 7/1990 | Felix | 604/27 |
| 4,968,298 | 11/1990 | Michelson | 604/36 |
| 4,983,160 | 1/1991 | Steppe | 604/22 |
| 5,053,011 | 10/1991 | Strobel et al. | 604/141 |
| 5,059,182 | 10/1991 | Laing | 604/141 |
| 5,064,168 | 11/1991 | Raines | 251/322 |
| 5,071,104 | 12/1991 | Witt et al. | 604/142 |
| 5,104,394 | 4/1992 | Knoepfler | 606/143 |
| 5,133,701 | 7/1992 | Han | 604/289 |
| 5,178,606 | 1/1993 | Ognier | 604/31 |
| 5,228,646 | 7/1993 | Raines | 251/95 |
| 5,228,647 | 7/1993 | Santome | 251/149.4 |

*Primary Examiner*—C. Fred Rosenbaum
*Assistant Examiner*—Frank Wilkens, III
*Attorney, Agent, or Firm*—Andrus, Sceales, Starke & Sawall

[57] ABSTRACT

An irrigation system includes an elongated, hand-held instrument for applying a solution spray to a surgical area of a patient during surgery. The instrument includes an elongated handle having an outer ribbed surface to be hand-held. The handle has a central passageway between an inlet end and a discharge end. A nose is secured to the discharge end of the handle with a flow control valve secured within the handle. Nozzles are selectively connected to the nose to create selected flow patterns at the surgical site. The valve has an external pushbutton actuator to control the solution flow through a passageway in the body and nose. A pressurized liquid supply includes a sealed disposable, liquid solution filled bag and a sterile tube connected to the inlet end of the body. The solution bag is releasably supported within a pressurizing bag which in turn is carried on a portable stand unit. A bulb pump or small pressurized cannister is coupled to the pressurizing bag, with a regulating valve, for establishing a pressure of about 100 to 600 mm therein. The irrigating solution flow is applied to the wound at about 8 to 15 psi. The solution bag, instrument and interconnected elements are all throw-away elements providing a sterile one-time irrigating apparatus.

14 Claims, 3 Drawing Sheets

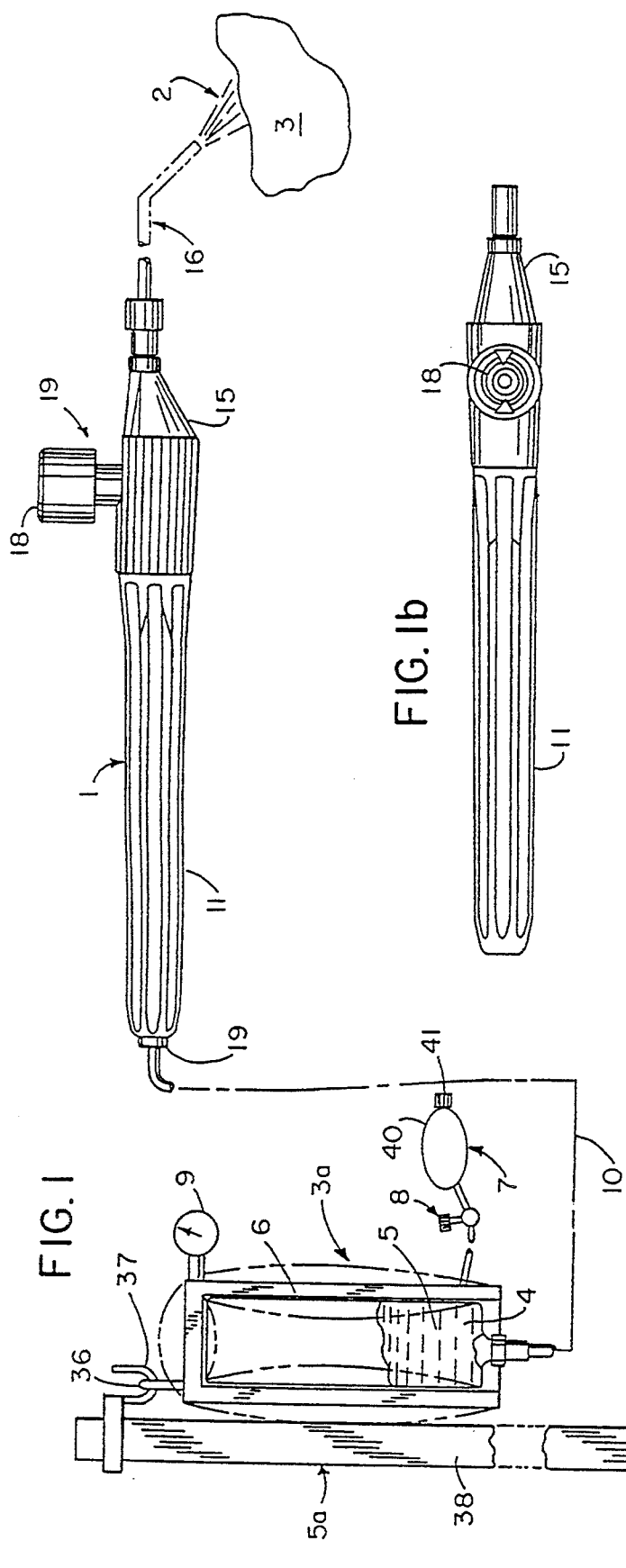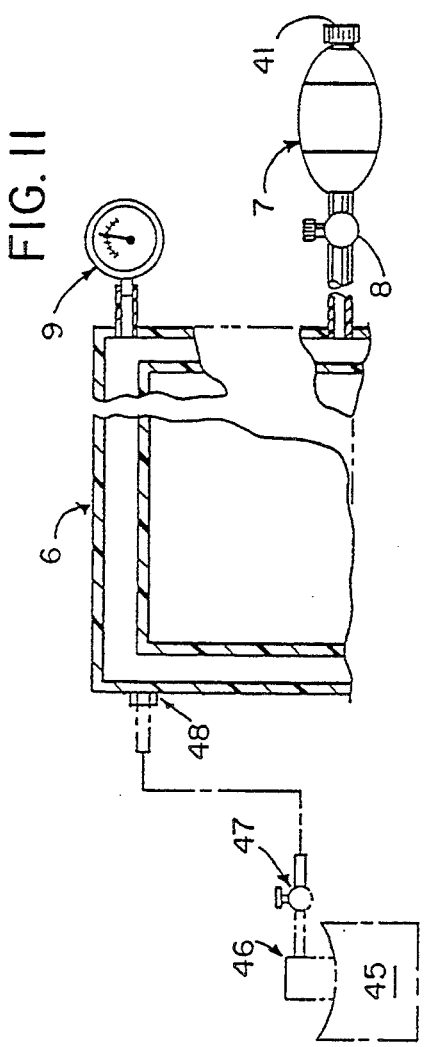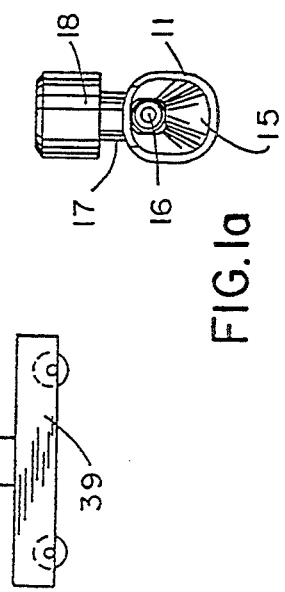

SURGICAL IRRIGATION APPARATUS FOR CLEANING AND STERILIZING WOUNDS AND SURGICAL AREAS DURING SURGERY

BACKGROUND OF THE INVENTION

The present invention particularly relates to an irrigation apparatus including a small, hand-held instrument for providing of a continuous or intermittent flow of cleaning and/or sterilizing liquid to a wound and particularly during various surgical procedures and particularly to such a hand-held instrument and apparatus having an appropriate regulated pressure and flow to insure proper functioning without damage to the patient's tissue.

During surgery, irrigation systems are provided for spraying the surgical area, including the patient's tissue and bones within the surgical area with an appropriate sterilizing and/or cleansing liquid solution. The solution further maintains a moist tissue to facilitate the surgical procedure and to optimize post surgical recovery. Often the instruments provided may also include an aspirating device for removal of blood, debris, excess fluid and the like. Such irrigation systems have also been suggested in connection with treatment of wounds generally prior to closure. The subject matter is discussed in some detail in a paper entitled "High-Pressure Wound Irrigation" and presented by Hal Rogness, R.N. BSN, ET, of Berkeley, Calif. in J. Enterostom Ther at a presentation on Dec. 27, 28, 1985. The paper presented includes a bibliography of various other publications relating to wound irrigation. As discussed in that reference, the present technology has considered three alternate methods of irrigation including a high pressure variety using a pulsating jet, and alternatively, a gravity drip application or a conventional bulb syringe application to the wound. A prior paper entitled "Evaluation Of Wound Irrigation By Pulsatile Jet And Conventional Methods" published in Volume 187, No. 2 of the American Surgical Journal in 1977 includes a statistical analysis with respect to the above three systems and no irrigation. As presented in the above papers, the general conclusion appears to be that the pulsating jet is a relatively high pressure jet providing good results in various applications but presents a continuing problem of possible tissue trauma. The papers also indicate that in the conventional methods described, adequate flow control and application of the solution while maintaining flow by the operator all present significant difficulties or problems in the field of irrigation, even though in practically all instances, irrigation is highly desirable and universally used. Various hand-held devices have also been suggested for delivery of the fluid to the wound area during surgery and the like. The various disclosures known to applicant all use powered liquid solution fluid sources such as generally discussed in the articles including wall mounted pressure and hand-held syringes with either a bulb pump or a plunger pump mechanism which are manually actuated to affect the surgical irrigation. Such units include hand-held syringe units which may have detachable nozzle members for delivering the fluid to limited areas by the operator during the surgical operation.

Thus, prior art patents have discussed various forms of surgical irrigating devices. A pressurized can device, for example, is disclosed in U.S. Pat. No. 5,133,701 which issued Jul. 28, 1992. In this patent, a small hand-held can type container is provided with an upper discharge valved nozzle. The can is pressurized, with discharge of the liquid through a valved nozzle. U.S. Pat. No. 5,178,606 discloses an irrigation and aspiration apparatus for application within a patient's remote cavity for endoscopic surgery, with a separate control for closely controlling the pressure and temperature of the liquid. The system establishes a hemostatic effect during the surgical process and thus provides a very specific application for a cavity surgical process. A pressurized system has also been disclosed to create a jet using a high pressure stream of appropriate sterilized saline solution to produce a cutting and knife action within the surgical area. For example, U.S. Pat. No. 4,913,698 which issued Apr. 3, 1990 discloses a high pressure jet device functioning as knife use during brain surgery. In this patent, a flexible container is housed within a high pressure container, with a nitrogen source coupled to the container to pressurize the container to a high level. The output is applied to a nozzle device having a small passage to generate a high pressure jet knife producing fine line incisions for crushing and removing brain tumors in cerebral surgery.

More recently, the present inventors have received information of a battery operated pumping system for delivery of a liquid solution for irrigating a wound area. Although identified as a throw-away unit, the unit is understood to cost about fifty dollars.

The most conventional method for wound irrigation is the hand-held syringe which has a limited volume of liquid and the pressure pump such as a piston or a bulb which is operated to directly generate a flow of liquid to the surgical area. The flow rate and pressure are of course directly related to and controlled by the particular skill of the operator in actuating of the pressurizing element. Thus, the operator's attention is directed to both creating the flow by operation of the syringe and directing the resulting flow into the required wound area. In addition, the syringe does not include a continuous solution source and must be periodically filled with the liquid solution.

Thus, various known systems provide hand-held tools which apply a liquid solution. However, each system has known difficulty in providing the desired pressure and flow application of the liquid to the wound area particularly during a surgical procedure.

In summary, hand-held jet devices have been widely used in surgical procedures for various reasons including those for applying a liquid to a wound. Generally, prior art wound moisturizing and cleansing device, however, include a drip bag, a syringe applicator or a pulsating jet device such as discussed above. The prior devices have been available for surgical procedures and the problems associated therewith known for many years.

There is therefore a significant need and demand for a simple, portable apparatus which can be supplied during a surgical procedure with a continuous flow of liquid solution from an assured source of the necessary solution while permitting the convenient and reliable functioning and operation of the apparatus by the operator.

SUMMARY OF THE PRESENT INVENTION

The present invention is particularly directed to a portable, compact system including a hand-held tool or instrument device for irrigation of the wound with the desired debridement and tissue moistening while providing of the fluid at an appropriate flow and pressure to prevent tissue damage and maintaining a high degree of portability and controlled solution application during a surgical procedure. Further, the solution container and instrument including all connections elements are readily constructed at a minimal cost and provide a cost effective disposable system for optimal safety. Generally, in accordance with the teaching of the present invention, the system includes a hand-held irrigating instrument connected to a conventional bag of appropriate solution such as a saline liquid or other suitable liquid. A pressurizing enclosing bag unit is coupled about the solution bag, and pressurized to apply pressure on the solution bag to a selected level, generally about in the range of 100 to 600 millimeters (mm) of mercury to produce a spray at the surgical area about in the range of eight to fifteen pounds per square inch (psi). The pressure level is controlled to establish a maximum starting pressure with such pressure available for the discharge of the essentially continuous supply of liquid solution during the surgical operation, and may be maintained through the use of a simple pressure regulating unit or the like. The pressurizing bag may be similar to that which has heretofore been used in connection with intervenous infusion devices in which a pressurized flow of the liquid or medication is fed to a needle embedded within a patient.

The irrigating instrument of the present invention is a throw-away, one time use device. In a preferred embodiment, a simple lightweight elongated handle having a tubular passageway ends in an applicating nozzle tip. The nozzle structure is preferably provided with a releasable nozzle connection to permit rapid removal and attachment of various nozzle tips appropriate to each particular wound and surgical procedure. The discharge end of the instrument may also provide connections for other auxiliary devices.

More particularly, in a commercial implementation, a simple elongated tubular hand-held instrument which terminates in a releasable end attachment for receiving of various nozzles tips. The outer surface is formed with recessed portion for convenient and reliable gripping in the operator's hand with a finger actuated flow control button. In a preferred construction the instrument is constructed to locate the control button to the side of the instrument for actuation by the thumb of the irrigator operator. The use of the thumb allows a more accurate control of the button position and thereby the flow control to the surgical area. The opposite end of the instrument includes a quick detachable coupling for direct coupling of the tube from a conventional saline or like solution bag such as presently used in intervenous applications. The flexible solution bag is placed within an open-ended pressure bag and supported by a suitable carrier such as the mobile carriers presently used for various patient infusion applications. A manually hand or foot actuated pump unit, such as a flexible bulb, is connected to the pressure bag for inflating the same and thereby pressurizing the solution bag. A pressure regulating device is preferably coupled to the pressure bag unit for presetting the pressure in the pressure bag and thereby within the solution bag. The pressurizing bag preferably has a significantly greater volume than the solution bag and thus maintains a continuous minimum pressure on the solution bag during the irrigating process. Alternatively, other bag pressurizing systems may be used. When continued pressure regulation is desired or necessary, a small pressurized can of $CO_2$ or nitrogen with a continuous pressure regulator may be coupled to the pressurizing bag. The hand-held instrument, in combination with the pressurizing bag and replaceable solution bag, provides all the advantages associated with portable intervenous feeding devices and the like while maintaining and providing the desired adjustable flow at the necessary safe pressure characteristic for maintaining optimal cleansing and/or sterilization of a wound and a surgical area. Thus, generally the pressure of a fluid applied will be controlled by the setting of the liquid filled bag while the flow characteristic is controlled by the finger actuated valve in the hand-held instrument which provides a simple on/off flow control as well as a flow level control.

The irrigating solution system includes throw-away components with an improved controlled solution application, and may be readily produced at a cost substantially in the range and competitive with the widely used syringe-type devices.

BRIEF DESCRIPTION OF THE DRAWINGS

The drawings furnished herewith illustrate a preferred embodiment of the present invention in which the above advantages and features are clearly disclosed as well as others which will be readily understood from the description of the illustrated embodiment.

In the drawings:

FIG. 1 is a schematic elevational view of a surgical irrigation apparatus constructed in accordance with the teaching of the present invention;

FIGS. 1a and 1b are front and side elevational views of the instrument shown in FIG. 1 without the nozzle attached;

FIG. 11 is a fragmentary enlarged view of a pressurizing bag illustrated in FIG. 1, with parts broken away and sectioned.

DESCRIPTION OF THE ILLUSTRATED EMBODIMENT

Figure 2:
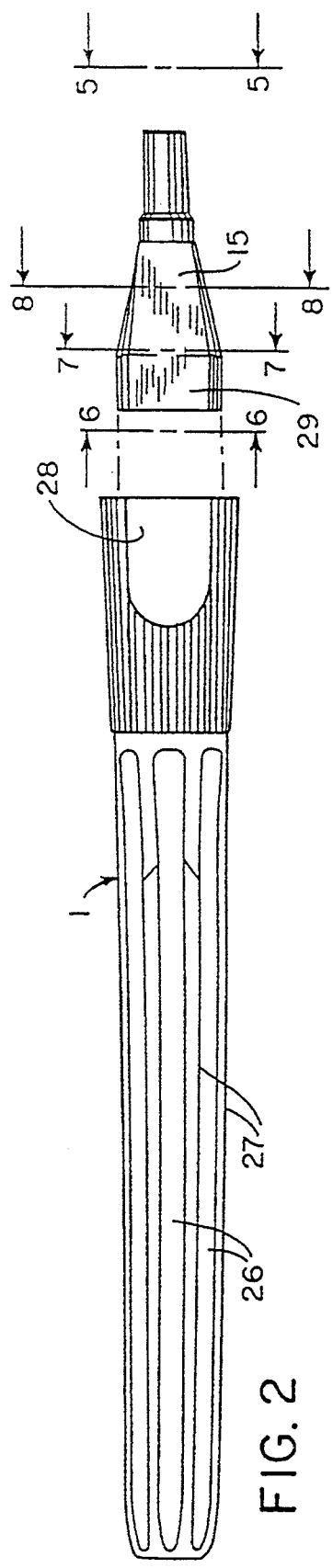
FIG. 2 is an exploded view of the hand-held instrument shown in FIG. 1 with the removable nose spaced from the instrument handle or body.

Referring to the drawings and particularly to FIG. 1, an irrigation instrument 1 is illustrated for applying a fluid spray 2 to a surgical area 3 during a surgical operation. The instrument 1 is a disposable, sterile unit which is designed for a single one-time use. The instrument 1 is connected to a pressurized liquid supply, which preferably includes a sealed disposable, and sterilized liquid solution bag 4 filled with an appropriate solution 5 for application to the wound or surgical area 3 of the patient. The bag 4 is a non-pressurized source of fluid which is releasably supported within a pressurizing bag 6 which in turn is carried on a portable stand unit 5a. A manual pump unit 7 is coupled to the flexible pressurizing bag 5 and is hand operated for pressurizing of the bag 5 and thereby the solution filled bag 4. A pressure regulator valve 8, such as a manually operable unit, is provided within the pressure connection or passageway from pump unit 7 to bag 6 to control the pressure level of the bag 6 and thereby bag 4. A readout unit 9 is provided for reading the pressure level when setting the pressure level by operation of the regulator valve 8. The liquid solution bag 4 is coupled through a tube 10 to the inlet end of the instrument 1. The present invention is directed to the supply of irrigating fluid to the surgical area and generally is limited to an applicating solution pressure at the area in the range of about 8 to 15 psi. The bag 5 may be set in the range of about 100 to 600 mm of mercury.

The pressurizing bag 6 is selected such that an appropriate pressure is maintained on the solution bag 4 during the discharge of the solution from the bag, thereby maintaining a relatively constant flow characteristic from the hand-held instrument. Typically, a pressurizing bag may have a volume on the order of two times the volume of the solution bag.

Figure 3:
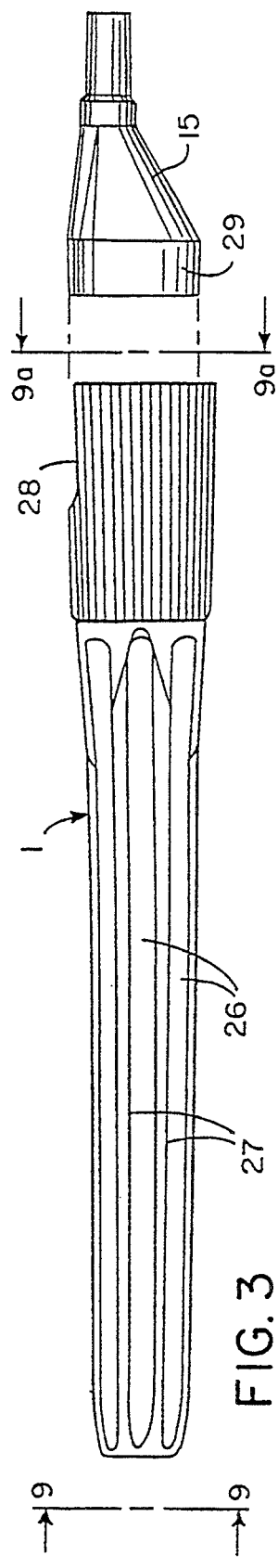
FIG. 3 is a top elevational view of FIG. 2.
Figure 4:
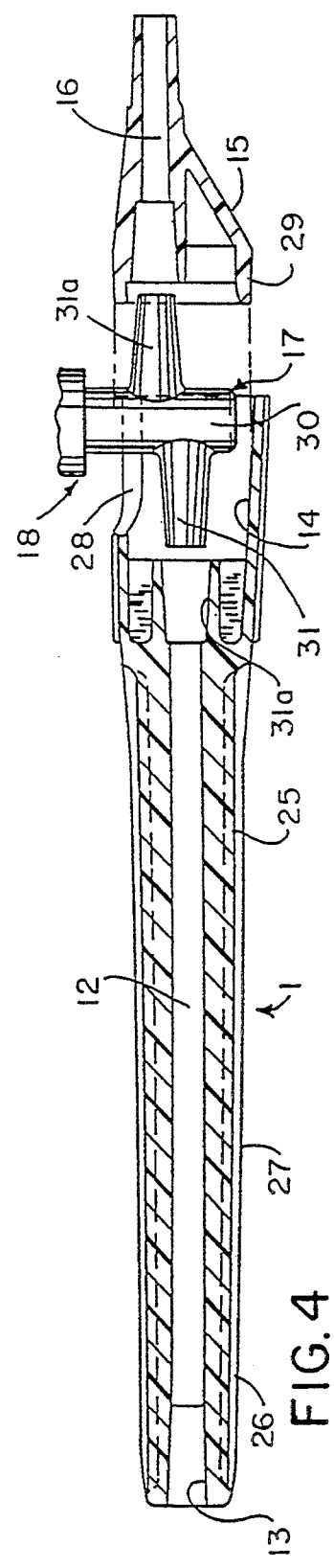
FIG. 4 is a longitudinal sectional exploded view through the hand-held tool or instrument shown in FIG. 1 with the valve unit shown partially in place.
Figure 5:
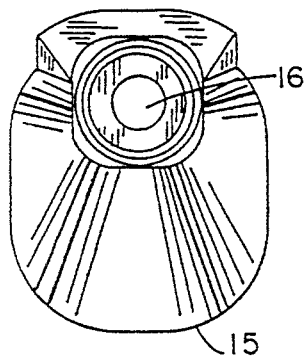
FIG. 5 is an end elevational view taken generally on lines 5—5 of FIG. 3.
Figure 6:
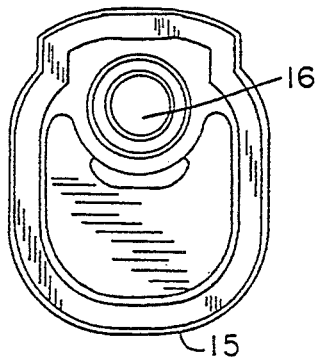
FIG. 6 is a vertical section taken generally on line 6—6 of FIG. 3.
Figure 7:
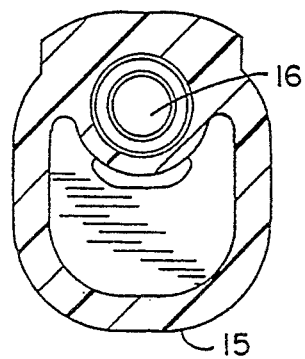
FIG. 7 is a vertical section taken generally on line 7—7 of FIG. 3.
Figure 8:
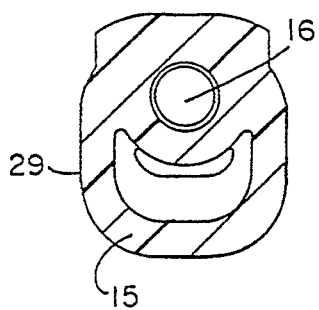
FIG. 8 is a vertical section taken generally on line 8—8 of FIG. 3.
Figure 9:
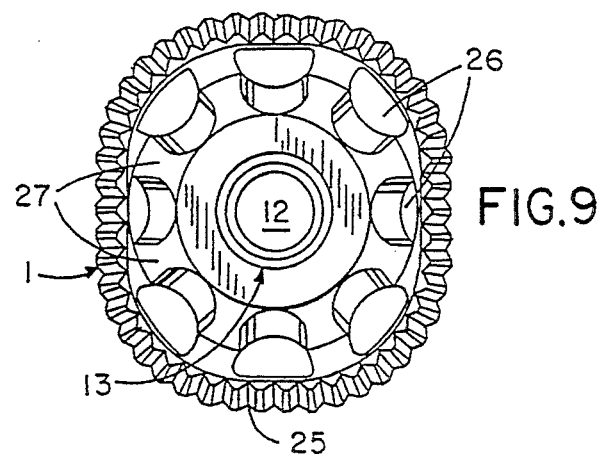
FIG. 9 is an end view taken generally on line 9—9 of FIG. 3.
Figure 9A:
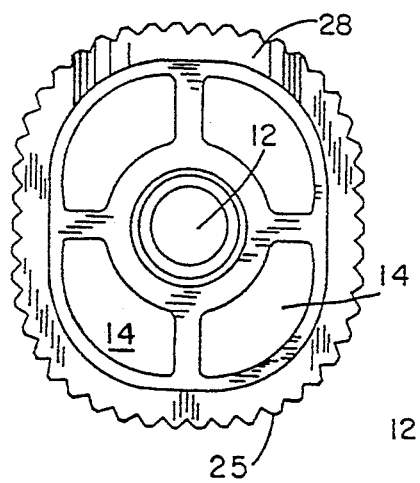
FIG. 9a is an end view taken generally on line 9a–9a of FIG. 3.

Referring particularly to FIGS. 2-4, the hand-held instrument generally includes a suitable elongated body member 11 forming a handle adapted to be grasped in the hand of the operator, such as the surgeon or his assisting personnel. The body member 11 has a central passageway 12 between an inlet end 13 connected to the tube 10 and a discharge end 14 at the opposite end. A discharge member or nose 15 is secured within the discharge end 14, with an offset passageway 16. A finger operated valve unit 17 is housed within the discharge end 14 between the passageways 12 and 16. The valve unit 17 includes an external pushbutton actuator 18 adapted to be operated by the finger, and preferably the thumb, of the operator. The valve unit 17 can be a simple on/off valve which opens and closes a valved passageway 18 between passageways 12 and 16 to provide a controlled liquid spray to the wound or surgical area 3 or to completely close off the flow. In operation, the solution bag 4 is located within the pressure bag 6 with bag 6 collapsed. The pressure unit 7 is hand actuated to inflate bag 6, thereby pressurizing the solution bag 4. The pressure regulator 8 is adjusted to the desired pressure. The instrument 1 is connected by the connecting line 10 to the inlet end of instrument 1 either before or after pressurization through a suitable quick connect system, such as a Leur connector 19. A nozzle tip 20 is similarly connected as by a Leur connector 21 to the instrument discharge end member or nose 15 which is then ready for use in the surgical room. The total assembly and manual pressurizing of the system can be completed within about one minute. The portable nature of the apparatus particularly adapts the apparatus for proper and optimum location within the surgical area while providing the improved pressurizing source to provide the desired pressurized flow from the instrument to the surgical area. The total system of the solution bag, the hand-held instrument and connecter elements can be provided at a cost of about three dollars. The low cost permits cost effective one-time use of the system.

During surgery, instrument 1 is hand-held with the valve button 18 as shown in FIG. 1 and thereby aligned with and engaged preferably by the operator's thumb, not shown. The appropriate spray 2 is applied with the desired flow rate and at a safe, non-damaging pressure to the tissue in the surgical area 2. The flow rate is controlled by thumb-operation of the pushbutton valve 17, and the pressure by the pressure unit 7 and level control valve 8. The irrigation solution is continuously available as required by the surgeon to provide optimum surgical conditions within the surgical area of the patient.

During surgery the tip or nozzle 20 can be readily and rapidly changed as desired. Following surgery, the solution apparatus including all components from and including bag 4 instrument 1, nozzles 20 and interconnecting tubing are disposed of through appropriate safety procedures in accordance with the known requirements and procedures.

More particularly, in the illustrated embodiment of the invention as shown in FIGS. 2-4, the instrument 1 is shown including a simple solid plastic body member or handle 11 having the central passageway 12 of a relatively constant diameter. The inlet end 13 is tapered to receive a suitable connector on the tube such as a Leur connector 19. The passageway extends generally co-axially through the body from the inlet end 13 to the discharge end 14.

The elongated instrument handle 11 is formed with a slightly increasing tapered outer wall surface to the discharge end 14, which is formed with a slightly greater outer diameter, as most clearly shown in FIGS. 2-4, to define the end chamber 14 for receiving the control valve 17 and the nozzle 15. The nose 15 is located to the outlet side of the finger-operated pushbutton valve unit 17. The first tapered portion of handle 11 is formed with a ribbed outer surface including a plurality of circumferentially spaced and longitudinally extended recesses and ridges 26 and 27. The ribbed outer surface construction provides for convenient and reliable grasping of the instrument by one hand of the operator. The outermost enlarged discharge end 14 has its outer surface formed with closely spaced longitudinally extended serrations 25. The upper wall of the discharge end 14 of handle 11 has an opening 28 within which the valve structure 17 is located and secured by the instrument nose 15 which extends into the enlarged discharged end.

Figure 10:
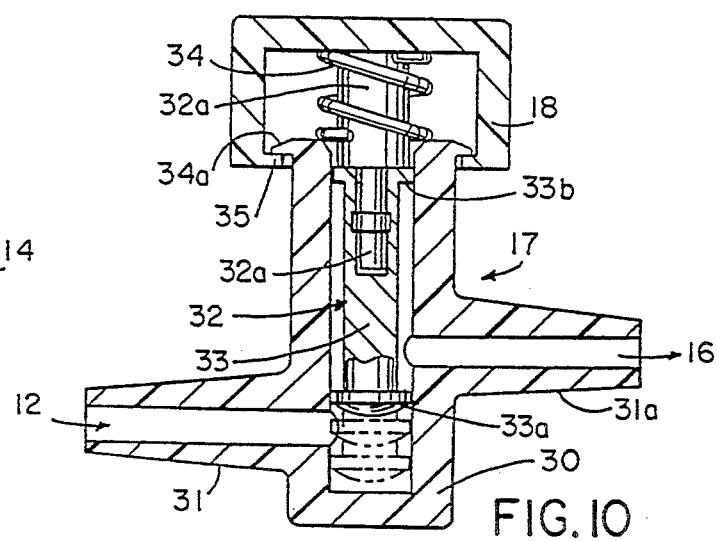
FIG. 10 is an enlarged longitudinal section through the valve structure shown in FIGS. 1 and 4.

The instrument nose 15 is a plastic body member having an enlarged portion with a tapered end 29 projecting into the chamber 14 which is correspondingly tapered. The nose 15 and the interconnected valve unit 17 is permanently secured within the discharged end through any suitable manner to form a sealed integral instrument, such as by a thermal bonding, a suitable adhesive or other suitable surface interconnecting system. The instrument nose 15 includes the offset discharge passageway 16. The inlet end of the passageway 16 is enlarged and is somewhat larger than the body passageway 12. The outer portion of the passageway 16 has a slightly smaller diameter than passageway of the instrument handle 11. The passageway 16 of the nozzle nose 15 is laterally offset from passageway 12 in accordance with the particular illustrated structure of valve unit 17, as more fully shown in FIGS. 4 and 10.

The valve unit 17 is clamped and sealed within the handle 11 by nose 15 as follows. The valve unit 17 includes a tubular body 30 closed at the inner end, and secured within the opening 14 of body member 11 with oppositely extended tubular connectors 31 and 31a aligned with passageway 12 and 16 respectively. The end chamber 14 of handle 11 has a connecting chamber mating with connecter 31 and nose 15 has a similar chamber connecter with connecter 31a in the assembled instrument 1 to firmly lock the valve body 30 within the instrument. A piston valve member 32 extends from within the pushbutton and is slidably journaled within a central opening connecting the tubular connectors 31 and 31a of the tubular body 30. The valve member 32 includes an inner elongated rubber body 33 secured to an outer rigid post 32a of member 32. The opposite ends of the rubber body 33 are enlarged sealing rings 33a and 33b slidably engaging the wall of body opening and adapted to be selectively aligned therein relative to the offset connectors 31 and 31a and thereby passageways 12 and 16. A spring 34 encircles the post 32a within the pushbutton 18. The spring 34 acts between an enlarged lip 34a of the outer end of the valve body 30, and biases the valve member 32 and button 18 outwardly to a closed position between connectors 31 and 31a and therefore passageways 12 and 16, as shown in full line illustration in FIG. 10. Button 18 is held to the valve body 30 by interlocking lips 35 projecting beneath the lip 34a. Depression of the button 18 and connected valve member 32 moves the inner valve ring 33a into the opening of valve connector 31 and thereby connects passageway 12 and 16. The outer valve ring 33b is held outside the tubular connector 31a and thereby restricts flow through the valve to connector 31a. A continuous flow through the instrument 1 to the outer nose is thereby created. Depression between a closed position and a full open or flow position, establishes a controlled partial flow. The extent of depressing button 18 thus controls the size of the opening and thereby the flow rate, as shown in phantom illustration in FIG. 10. The valve unit 17 is shown and more fully described in U.S. Pat. No. 5,064,168 which issued Nov. 12, 1991 and U.S. Pat. No. 5,228,646 which issued Jul. 20, 1993.

The nozzle or tip 20 is shown as a simple tubular member which is releasably coupled to the outlet end of the instrument 1 and particularly the passageway 16 of nose 15. In the illustrated embodiment of the invention, a simple interconnection such as a Leur connector is illustrated in FIG. 1. The openings to passageways 12 and 16 may thus be formed with a small lip, not shown, to provide a positive interlocking connection such as with known Leur connections.

The small hand-held instrument 1 with the pushbutton control, provides a simple controlled flow of the liquid solution, as at 2 of FIG. 1. The inlet end 13 of passageway 12, of course, is directly coupled to the solution bag 4 while the passageway 16 of discharge nose 15 is connected to the appropriate spray nozzle 20 to create a desired solution flow 2 such as a concentrated jet, a dispersed jet or the like, all under a controlled and essentially continuous pressure and flow characteristic, as controlled by proper operation of valve 17 and the regulating system of the pressurizing bag system.

More particularly in the illustrated embodiment of the invention, the solution bag 4 is preferably the conventional bag widely used for intervenous feeding of liquid to a patient. The pressurizing source 3a includes the bag member 6 which may correspond to the bags presently used for pressurized intervenous feeding of medication to a patient. The pressurized bag 6 is shown formed with an apertured flange 36 which hangs on a hook 37 of the support 5a. Support 5a is shown as a typical mobile unit having a support post 38 attached to a wheeled base 39. Hook 37 is secured to the top of post 38. The pump unit 7 is shown as a conventional well known flexible bulb 40 having an inlet valved opening 41 and an outlet tube 4 with regulating valve 8 secured therein. Compressing and releasing of the bulb 40 results in pressurizing of the bag 6. Thus, air flows into the inlet valved opening 41 and upon compression of the bulb 40, the inlet closes 41 and the air flows outwardly into the pressurizing bag 5. Valve 8 is an adjustable valve unit to release the pressure from the bag and thereby preset the pressure at the desired level. During operation, the bulb 40 may be actuated to reset the pressure as desired using the pressure gage 9 to monitor the pressure level.

In a practical implementation of the present invention, the instrument had a length of approximately five inches and a diameter of approximately one-half inch at the outer end of the valve body. The nose had a length of about one inch. Passageway 12 had a diameter of approximately 0.115 inches, with a two degree increasing taper from the inlet end to the outlet end. The nose passageway 16 had a diameter of approximately 0.090 inches with reducing taper from the inlet to the outlet end.

Thus, although shown in a specific embodiment, various variations can, of course, be provided within the teaching of providing a low cost, throw-away solution instrument and system for irrigation flow in surgical procedures. For example, as shown in phantom in FIG. 10, a small pressurized cannister 45 carbon dioxide ($CO_2$) or nitrogen ($N_2$) may be connected to the pressurizing bag 6. The cannister output unit 46 includes an adjustable self-regulating control unit 47, with the output unit 46 connected to the bag inlet 48. A continuous regulated pressure is maintained in bag 6 and thereby in solution bag 4. The surgical instrument may also be provided for removal of liquids and debris from the wound area such as by having additional suction passageway for removal of the same. Further, the saline bag and the pressure bag may take different forms but generally require the simple use of a throw-away bag in combination with a simple, pressurizing chamber member connected to a manually actuated pump unit or other form of pressurizing means for pressurization of the solution bag. The solution system includes totally disposable components consisting of the sterile solution bag and the sterile instrumentations as well as all interconnected components. The present invention thus provides a simple, and relatively inexpensive surgical irrigating apparatus. The apparatus is readily and rapidly assembled at the operating site without the necessity of special skills or instrumentations while maintaining a highly satisfactory application of a cleansing and/or sterilizing liquid to a surgical wound area.

The present invention with the convenient throw-away construction provides a conveniently manipulated and hand-held instrument. The finger tip and particular thumb control permits adjustment of the flow in a precise manner, with the pressure set at the level to minimize any tissue injury while permitting uninterrupted and continuous irrigation. The simplicity of the system including the disposable solution bag and the disposable instrument provides a sterile apparatus which can be readily constructed for cost effect one-time use. The system with a pressurizing bag unit also provides a convenient and rapid apparatus for assembly of the irrigation system. The irrigation system can be located in spaced relation to the patient and out of the surgeon's field of view. Finally, the simplicity of the instrument unit particularly provides for disposing after each surgical procedure for maximum patient and personnel safety.

The present invention may be used in various surgical procedures to maintain tissue moisture and with an appropriate flow without the undesirability deluge of flow associated with bulb syringes and the like. The system can be readily applied in microsurgery where precision irrigation and adjustable flow is often required. In other surgical procedures, such as ophthalmic and orbital surgery, the system provides for repeated irrigation at adjustable pressure and flow as a result of rapid setting of the pressure level and adjusting the flow with the finger controlled irrigator. In maxillofacial and oral surgery, it is necessary to pin point irrigation and it is established without tissue desiccation and/or heat injury to the tissue. The adjustable flow characteristic also particularly adapts the unit to orthopedic and hand surgery and particularly during bone drilling and plating to further prevent tissue injury. The very simple disposable single use irrigator tool and system of the present invention particularly adapts the unit to the present surgical systems in various surgical facilities to establish and maintain optimal surgical environment.

Various modes of carrying out the invention are contemplated as being within the scope of the following claims particularly pointing out and distinctly claiming the subject matter which is regarded as the invention.

We claim:

1. A hand-held disposable surgical irrigating apparatus for irrigation of a surgical site with a low pressure stream of a liquid solution during surgery including macrosurgical and microsurgical procedures, comprising a lightweight elongated hand-held irrigating instrument for grasping between the fingers for manipulation and positioning relative to the surgical site and having an inlet end and a discharge end for establishing an irrigating solution stream to said surgical site during a surgical procedure, a flexible bag of an irrigating liquid solution having a sealed outlet, a connecting tube element connecting the sealed outlet of said bag to said inlet end, a pressurizing member substantially enclosing the solution bag, a pressurizing unit coupled to said pressurizing member to pressurize the pressurizing member and thereby said solution bag, said instrument including a body member with a solution inlet passageway and a solution outlet passageway spaced from the inlet passageway and forming a valve opening, a flow control valve secured within said valve opening in said body member and defining a coupling passageway between said inlet passageway and said outlet passageway, said control valve having a finger-actuated control member located within said valve opening with an external pushbutton operator for engagement by the finger of the personnel operating the irrigating apparatus for establishing a steady state stream of irrigating liquid solution, said control valve being located adjacent to said discharge end and mounted for variable positioning of said control member in said opening, said control member being continuously positioned within said valve opening between a first position and a second position to vary said opening during a surgical procedure and the rate of flow of said steady state stream of said irrigating liquid solution at a pressure preventing damage to the patient within the surgical site while maintaining optimal desired flow for required cleansing, moisturizing and sterilization at the surgical site contributing to improved surgical results, and said solution bag and said instrument and all flow connecting tube elements forming a throw-away assembly for one time use for maintaining maximum barsty in the surgical equipment, at least two nozzle tips for establishing at least two different streams, each said tip having an identical end attachment unit, and said discharge end of said instrument having a quick tip coupling unit for receiving said end attachment unit for rapid replacement of said nozzle tips during a surgical procedure.

2. The irrigating apparatus of claim 1 wherein said instrument includes a lightweight and elongated plastic handle including said inlet passageway as a straight tubular passageway ending in an open chamber, a nozzle-receiving nose secured within the outer end of said chamber and having an outer end constructed for selective releasable attachment of one of said nozzle tips to said receiving nose and said nose having a straight passageway, said plastic handle having a top and bottom and sides, said solution outlet passageway and said control valve including a valve body clamped between said plastic handle and said nose with a fluid tight connection and with tubular connectors aligned with said inlet passageway and said discharge passageway, said control member including said pushbutton operator extending laterally into a side of said body and oriented for engagement by the thumb of the operator's hand.

3. The apparatus of claim 1 wherein said pressurizing member is a flexible bag connected to said solution bag and including a continuous pressure regulating valve unit.

4. The apparatus of claim 1 wherein said pressurizing member is a small pressurized container having said pressurized bag at a selected pressure.

5. The irrigating apparatus of claim 1 wherein said instrument has a length on the order of five inches and a maximum diameter on the order of one-half inch.

6. The irrigating apparatus of claim 5 wherein said body member includes an inlet body element including said inlet passageway and an outer nose element including said outlet passageway and being telescoped with said body member and interconnected to each other, said control valve including a valve body clamped between said body element and said nose element.

7. The apparatus of claim 6 wherein said body element includes an outer surface formed with a circumferentially spaced and longitudinally extended recessed portion for convenient and reliable hand gripping of the instrument with a finger of operator's hand overlying said control member.

8. A hand-held and disposable irrigating instrument for applying a liquid solution from a pressurized liquid supply to a surgical site of a patient during surgery, comprising an elongated tubular handle for grasping between the fingers by the irrigating personnel for hand-held operation and positioning and having a central passageway between an inlet end and a discharge end, a tubular nose member secured to said discharge end of said tubular handle and extending longitudinally therefrom and having a straight discharge passageway offset from said central passageway and extending to a discharge coupling unit, a flow control valve sealed between said tubular handle and said tubular nose member, said coupling unit includes a connector unit for selectively and releasably receiving a nozzle tip to create a selected flow pattern at the surgical site, said flow control valve having a connecting flow passageway connecting said central passageway to said discharge passageway and a flow control member located within said connecting flow passageway and mounted for continuous movement within the connecting flow, passageway to adjust the degree of the opening of the connecting flow passageway between a fully opening and fully closed position to form a steady state stream of solution, and an external finger-operated pushbutton actuator connected to said flow control member for continuous positioning said control member within said connecting passageway and thereby establishing and adjusting the degree of the opening and thereby the flow rate of said continuous steady state stream of solution through said handle and nose member from a pressurized liquid supply of said liquid solution for optimal supply of liquid solution to the wound during the surgery.

9. The irrigating instrument of claim 8 wherein said tubular body and nose member have a total length on the order of five inches and a diameter on the order of one-half inch.

10. The irrigating instrument of claim 8 wherein valve includes a valve body, and wherein said handle, said nose members and said valve body are each a molded plastic element and are joined to each other to form a continuous integral body unit.

11. A disposable hand-held and operated irrigating instrument adapted to be grasped between the fingers of irrigating personnel for applying a liquid solution stream to a surgical site of a patient during surgery and adapted to receive a plurality of different flow tips each of which can establish a selected flow stream to the surgical site, comprising an elongated tubular handle having an inlet end and a discharge end and a central passageway therebetween, a tubular nose having an inlet end connected to said discharge end of said tubular handle and extending longitudinally therefrom, said handle and said tubular nozzle having said connected ends including telescoped end portions for firmly interconnecting of said handle and said tubular nose with said tubular nose extending in said longitudinal direction, said nose having a straight discharge passageway laterally offset from said central passageway and terminating in a discharge end including a slip fit coupling adapted to receive each of said nozzle tips, said telescoped end portions of said handle and said nose defining an internal valve chamber, a flow control valve unit located within said valve chamber and having first and second passageway members aligned with said inlet passageway of said handle and said discharge passageway of said nose with a valve opening connecting said first and second valve passageways, a valve member located within said valve opening and selectively positioned with a continuous movement through the valved opening to variably open and close said valved opening and thereby control the flow rate through said valve unit into said discharge passageway and tip, said valve member having an operator member projecting substantially laterally outwardly of said handle and tubular nose and terminating in an external finger operated pushbutton, said valve member being resiliently loaded to one of said opened and closed position and selectively and continuously movable therebetween by the finger of the operator between said opened and closed position and thereby producing a continuous varying opening between said positions and producing an adjustable steady state stream of said liquid solution from said tubular nose and tip and thereby establishing optimal stream of the liquid solution at any selected flow rate between a fully open position and fully closed position of said valve during a surgical procedure.

12. An irrigating instrument of claim 11 having a valve opening extending perpendicular between said inlet and discharge passageways, said valve member having a first position located between said inlet and outlet passageways and movable selectively through one of said passageways to selectively open the valve opening between said passageways.

13. The irrigating instrument of claim 12 wherein said valve member includes a valve body having a centrally located tubular portion closed at one end and having said inlet and outlet members formed as axially offset passageway members integral with said valve body and projecting in diametrically opposite directions from opposite sides of said valve body, said inlet and outlet members being spaced in accordance with the inlet passageway of the handle and the discharge passageway of the nose and projecting into said respective passageways, said valve member being slidably mounted within said valve body and projecting outwardly therefrom with a sealed coupling, said valve member having an inner head corresponding to the diameter of said valve opening and a stem portion projecting outwardly whereby movement of the head within the opening between said inlet and outlet passageways seals the flow therethrough and movement of said valve member and movement through said head through one of said inlet and outlet passageways selectively opens and closes said opening between said passageways and adjusts said flow rate therethrough.

14. The irrigating instrument of claim 13 wherein said handle structure includes a head portion adapted to receive said nose and located for convenient grasp in the fingers of the user, and an extended handle portion extending rearwardly from said head portion and forming a substantial length of said handle structure, whereby the head portion is adapted to be gasped by the fingers of the operator with the handle extending rearwardly through the hand.

* * * * *

UNITED STATES PATENT AND TRADEMARK OFFICE
CERTIFICATE OF CORRECTION

PATENT NO. : 5,419,772
DATED : May 30, 1995
INVENTOR(S) : TEITZ ET AL

It is certified that error appears in the above-identified patent and that said Letters Patent is hereby corrected as shown below:

Column 10, claim 1,
Line 7, delete "barsty" and insert ---safety---; CLAIM 8, Column 11, Line 6, after "flow" delete "," (comma).

Signed and Sealed this

Tenth Day of October, 1995

*Attest:*

BRUCE LEHMAN

*Attesting Officer*   *Commissioner of Patents and Trademarks*